(12) United States Patent
Morlacchi et al.

(10) Patent No.: US 8,394,890 B2
(45) Date of Patent: Mar. 12, 2013

(54) COSMETIC COMPOSITION COMPRISING A POLYURETHANE BASED ON DIALKYL TARTRATE DIOL AND USES THEREOF

(75) Inventors: Simona Morlacchi, Roncello (IT); Anika Salanti, Milan (IT)

(73) Assignee: Intercos S.p.A., Milan (IT)

( * ) Notice: Subject to any disclaimer, the term of this patent is extended or adjusted under 35 U.S.C. 154(b) by 0 days.

(21) Appl. No.: 13/126,427

(22) PCT Filed: Oct. 29, 2009

(86) PCT No.: PCT/EP2009/064272
§ 371 (c)(1),
(2), (4) Date: Jul. 8, 2011

(87) PCT Pub. No.: WO2010/049480
PCT Pub. Date: May 6, 2010

(65) Prior Publication Data
US 2011/0262376 A1    Oct. 27, 2011

(30) Foreign Application Priority Data
Oct. 31, 2008 (IT) .............................. MI2008A1925

(51) Int. Cl.
*C08L 75/06* (2006.01)
*A61K 8/02* (2006.01)

(52) U.S. Cl. ............ 524/590; 424/401; 424/64; 424/69; 424/70.1; 428/423.1

(58) Field of Classification Search .................. 524/590; 424/401, 64, 69, 70.1; 428/423.1
See application file for complete search history.

(56) References Cited

U.S. PATENT DOCUMENTS

| | | | |
|---|---|---|---|
| 4,743,673 A | 5/1988 | Johnston et al. | |
| 6,177,523 B1 | 1/2001 | Reich et al. | |
| 2002/0076425 A1 | 6/2002 | Mondet et al. | |

FOREIGN PATENT DOCUMENTS

EP    1588686 A    10/2005

OTHER PUBLICATIONS

Okamoto, et al. Manufacture of polyurethanes for medical goods and optical resolution reagents XP-002541520; Database CA [Online] Chemical Abstracts Service, Columbus, OH, Feb. 6, 1988 (1 page).
International Search Report and Written Opinion issued in International Application No. PCT/EP2009/064272 dated Oct. 28, 2010 (12 pages).

*Primary Examiner* — Gina C Justice
(74) *Attorney, Agent, or Firm* — Novak Druce Connolly Bove + Quigg LLP

(57) ABSTRACT

Cosmetic composition comprising, as film-forming agent, an aliphatic polyurethane based on dialkyl tartrate diol in a mixture of organic solvents and cosmetically acceptable ingredients.

19 Claims, No Drawings

COSMETIC COMPOSITION COMPRISING A POLYURETHANE BASED ON DIALKYL TARTRATE DIOL AND USES THEREOF

FIELD OF THE INVENTION

The present invention relates to a composition comprising a polyurethane based on dialkyl tartrate diol and to its use in cosmetic products.

More in particular, the present invention relates to a cosmetic composition comprising, as film-forming agent, an aliphatic polyurethane based on dialkyl tartrate diol in a mixture of organic solvents, and to its use in cosmetic products for the skin of face, eyes and lips.

BACKGROUND OF THE INVENTION

The use of various polymers having filming properties in solution with an organic solvent is known in the field of cosmetics. Typical examples of these polymers are inter alias polyacrylates, and in particular silicone polyacrylates, polyesters, polyvinylpyrrolidone, polyisoprene and polyurethanes, in particular silicone polyurethanes.

Indeed, the use of film-forming aliphatic and/or cyclic aliphatic polyurethanes having a base of poly(dimethyl siloxane) diols (polydimethiconols) in cosmetic formulations, such as liquid lipstick, eye shadows and mascara, is known (US 2005/0238611).

The cosmetic products obtained from these polydimethiconol-based polyurethanes have however many drawbacks.

Indeed, these cosmetic formulations which employ polydimethiconol-based polyurethanes as film-forming agents have an opaque appearance, i.e. they are not provided with the features of brilliancy required for a cosmetic product for the skin of face and lips, are sticky and thus not comfortable on the skin of face, eyes and lips, and have a high cost for manufacturing the polydimethiconols themselves.

The use of polymers having filming properties, such as polyacrylates, silicone polyacrylates, polyesters and polyisoprenes in isododecane in cosmetic formulations is also known. GIOVAREZ® BTB-50 (i.e. 50% behenyl methacrylate/tert-butyl methacrylate copolymer solution in isododecane) from Phoenix Chemical, Inc. and KP 550 (i.e. 40% acrylate/modified silicone copolymer solution in isododecane) from Shin Etsu Chemical Corporation Ltd may be mentioned among the marketed products belonging to the above families. These products however have bad-smelling, irritating residual monomers, in addition to a high manufacturing cost.

Polyurethane polymers obtained by employing dialkyl tartrate diols in combination with aromatic glycols and aromatic isocyanates are also known (JP 1970519). These products have excellent chemical-physical properties, are biocompatible and used in the medical field. However, no products belonging to the aforesaid family for cosmetic applications are known.

DETAILED DESCRIPTION AND EXAMPLES

The technical problem underlying the present invention is thus to provide a cosmetic composition adapted to be used on the delicate, sensitive skin of face, eyes and lips which does not have the aforesaid drawbacks while having the required features of a cosmetic product, such as brilliancy, manual application ease, good film-forming properties, being long-lasting, conferring good sensory properties, being transfer-resistant and fast-drying.

The applicant conducted many experimental tests before selecting a particular polyurethane solution capable of conferring all the aforesaid features to the cosmetic composition which contains it.

It is thus a first object of the present invention a cosmetic composition comprising, as film-forming agent, an aliphatic polyurethane based on dialkyl tartrate diol in a mixture of organic solvents and cosmetically acceptable ingredients.

In a first embodiment of the present invention, said aliphatic polyurethane based on dialkyl tartrate diol may be obtained by the process comprising the steps of reacting a dialkyl tartrate diol, wherein the dialkyl group has equal or different from each others, linear or branched alkyl groups having from $C_{10}$ to $C_{20}$ carbon atoms, with an aliphatic diisocyanate selected from the group consisting of isophorone diisocyanate, 1,6-hexamethylene diisocyanate and 4,4'-dicyclohexylmethane diisocyanate, in an organic solvent.

In a second embodiment of the present invention, said aliphatic polyurethane based on dialkyl tartrate diol may be obtained by the process comprising the steps of reacting a dialkyl tartrate diol, wherein the dialkyl group has equal or different from each others, linear or branched alkyl groups having from $C_{10}$ to $C_{20}$ carbon atoms, and a natural polyol, with an aliphatic diisocyanate selected from the group consisting of isophorone diisocyanate, 1,6-hexamethylene diisocyanate and 4,4'-dicyclohexylmethane diisocyanate, in an organic solvent.

Preferably, the equivalents ratio from diol and diisocyanate ranges from 1.5 and 0.5 in the first or second embodiment of the present invention, even more preferably from 1.2 to 0.8.

The mixture of organic solvents of the cosmetic composition is preferably selected from the group consisting of a binary mixture of isododecane and ethanol, paraffin and ethanol, and isoparaffin and ethanol. Even more preferably, said mixture of organic solvents consists of isododecane and ethanol.

The ethanol in said mixture of organic solvents is advantageously present in an amount from 1% to 15% by weight, even more advantageously ethanol is present in an amount of 10% by weight.

Said dialkyl group of said dialkyl tartrate diol in the first or second embodiment of the present invention advantageously has linear or branched alkyl groups having from $C_{11}$ to $C_{15}$ carbon atoms. Even more advantageously, said dialkyl group of said dialkyl tartrate diol has linear alkyl groups different from one another having $C_{12}$ and $C_{13}$ carbon atoms.

A preferred example of diisocyanate is isophorone diisocyanate.

A preferred example of said natural polyol present in the second embodiment of the present invention is selected from the group consisting of hydrogenated dilinoleyl alcohol, partially dehydrated and hydrogenated at hydroxylic functionality of 2 castor oil, dimer diols derived from $C_{36}$ acids and dimerates. Even more preferably, said polyol is hydrogenated dilinoleyl alcohol or partially dehydrated and hydrogenated at hydroxylic functionality of 2 castor oil.

Said aliphatic polyurethane based on dialkyl tartrate diol of the first or second embodiment of the present invention is advantageously present in an amount from 25% to 55% by weight in the organic solvent. Even more advantageously, it is present at a concentration from 35 to 45% in the organic solvent.

Said organic solvent present in the first or second embodiment of the present invention is preferably isododecane.

The applicant surprisingly found that the cosmetic composition of the present invention as described above is provided with excellent film-forming properties, is easy to be applied, confers brilliancy to the zone where it is applied and is transfer-resistant.

Therefore, it is a second object of the present invention the use of the cosmetic composition as described above in a cosmetic product for the skin of face, eyes and lips.

Said cosmetic product is preferably selected from the group consisting of eye shadow, eye liner, eye mascara, foundation and pigmented face powders, and lipsticks.

The following examples are provided to illustrate the present invention without limiting it in any manner.

Example 1

Preparation of an Aliphatic Polyurethane Based on Dialkyl Tartrate Diol of the Invention

| Components | Parts by weight |
|---|---|
| Phase A | |
| isododecane | 540.00 |
| $diC_{12}$-$C_{13}$ alkyl tartrate | 218.65 |
| zinc stearate | 1.10 |
| Phase B | |
| isophorone diisocyanate | 95.25 |
| isododecane | 45.00 |
| Phase C | |
| pure ethyl alcohol | 100.00 |

Phase A, consisting of 540.00 parts by weight of isododecane, 218.65 parts by weight (equivalent weight=250.00 g/equiv. 0.87460 equivalents) of di-$C_{12}$-$C_{13}$ alkyl tartrate sold under the trade name of COSMACOL ETI Low Odour by SOSOL Italia S.p.A. (IUPAC: butanedioic acid, 2,3-dihydroxy-[R—(R*,R*)]-, linear and branched $C_{12}$-$_{14}$-alkyl esters) and 1.10 parts by weight of zinc stearate, was loaded in a five-neck reactor equipped with a condenser, a dropper funnel, a thermometer, a nitrogen inlet and a stirring system.

Under stirring, the system temperature was raised to 95° C., under nitrogen flow, and Phase B consisting of 95.25 parts by weight (equivalent weight=111.15 g/equiv., 0.85695 equivalents) of isophorone diisocyanate and 45.00 parts by weight of isododecane was added to the aforesaid Phase A.

The reaction mixture thus obtained was heated at 95° C. for 15 hours and continued until complete disappearance of isocyanate groups. The absence of free NCO groups was detected by means of FTIR.

The obtained solution was then cooled to 70° C. and diluted with Phase C. consisting of 100.00 parts by weight of pure ethyl alcohol BG 96 and the whole was heated at 80° C. for further 2 hours.

The solution was then cooled to 40° C. and filtered through a steel filter.

A transparent polyurethane solution containing a di-$C_{12}$-$_{13}$ alkyl tartrate was thus obtained. Such a polyurethane had a molecular weight of 30,000 daltons, a viscosity of 2000 mPa*s (at 25° C.) and a concentration of 31.50% by weight.

Example 2

Preparation of an Aliphatic Polyurethane Based on Dialkyl Tartrate Diol of the Invention

| Components | Parts by weight |
|---|---|
| Phase A | |
| isododecane | 391.50 |
| $diC_{12}$-$C_{13}$ alkyl tartrate | 273.02 |
| zinc stearate | 1.53 |
| hydrogenated dilinoleyl alcohol | 29.60 |
| Phase B | |
| isophorone diisocyanate | 130.85 |
| isododecane | 43.50 |
| Phase C | |
| pure ethyl alcohol | 130.00 |

Phase A, consisting of 391.50 parts by weight of isododecane, 273.02 parts by weight (equivalent weight=250.00 g/equiv. 1.09420 equivalents) of di-$C_{12}$-$C_{13}$ alkyl tartrate sold under the trade name of COSMACOL ETI Low Odour by SOSOL Italia S.p.A. (IUPAC: butanedioic acid, 2,3-dihydroxy-[R—(R*,R*)]-, linear and branched $C_{12}$-$_{14}$-alkyl esters) and 1.53 parts by weight of zinc stearate and 29.60 parts by weight (equivalent weight=267.20 g/equiv., 0.11078 equivalents) of hydrogenated dilinoleyl alcohol sold under the trade name of PRIPOL 2030 by Uniquema International, was loaded in a five-neck reactor with a condenser, a dropper funnel, a thermometer, a nitrogen inlet and a stirring system.

Under stirring, the system temperature was raised to 95° C., under nitrogen flow, and Phase B consisting of 130.85 parts by weight (equivalent weight=111.15 g/equiv., 1.17724 equivalents) of isophorone diisocyanate and 43.50 parts by weight of isododecane was added to the aforesaid Phase A.

The reaction mixture thus obtained was heated at 95° C. for 15 hours and continued until complete disappearance of isocyanate groups. The absence of free NCO groups was detected by means of FTIR.

The obtained solution was then cooled to 70° C. and diluted with Phase C consisting of 130.00 parts by weight of pure ethyl alcohol BG 96 and the whole was heated at 80° C. for further 2 hours.

The solution was then cooled to 40° C. and filtered through a steel filter.

A transparent polyurethane solution containing a di-$C_{12\text{-}13}$ alkyl tartrate in isododecane was thus obtained. Such a polyurethane had a molecular weight of 45,000 daltons, a viscosity of 1250 mPa*s (at 25° C.) and a concentration of 43.50% by weight.

Example 3

Preparation of an Aliphatic Polyurethane Based on Dialkyl Tartrate Diol of the Invention

| Components | Parts by weight |
| --- | --- |
| Phase A | |
| isododecane | 405.00 |
| diC$_{12}$-C$_{13}$ alkyl tartrate | 273.55 |
| zinc stearate | 1.57 |
| hydrogenated castor oil at fOH = 2 | 43.77 |
| Phase B | |
| isophorone diisocyanate | 131.11 |
| isododecane | 45.00 |
| Phase C | |
| pure ethyl alcohol | 100.00 |

Phase A, consisting of 405.00 parts by weight of isododecane, 273.55 parts by weight (equivalent weight=250.00 g/equiv. 1.09420 equivalents) of di-C$_{12}$-C$_{13}$ alkyl tartrate sold under the trade name of COSMACOL ETI Low Odour by SOSOL Italia S.p.A. (IUPAC: butanedioic acid, 2,3-dihydroxy-[R—(R*,R*)]-, linear and branched C$_{12-14}$-alkyl esters) and 1.57 parts by weight of zinc stearate and 43.77 parts by weight (equivalent weight=400.00 g/equiv., 0.10942 equivalents) of hydrogenated castor oil at fOH=2 sold under the trade name of POLYCIN D-140 by Vertellus Performances Materials Inc, was loaded in a five-neck reactor with a condenser, a dropper funnel, a thermometer, a nitrogen inlet and a stirring system.

Under stirring, the system temperature was raised to 95° C., under nitrogen flow, and Phase B consisting of 131.11 parts by weight (equivalent weight=111.15 g/equiv., 1.17958 equivalents) of isophorone diisocyanate and 45.00 parts by weight of isododecane was added to the aforesaid Phase A.

The reaction mixture thus obtained was heated at 95° C. for 15 hours and continued until complete disappearance of isocyanate groups. The absence of free NCO groups was detected by means of FTIR.

The obtained solution was then cooled to 70° C. and diluted with Phase C consisting of 100.00 parts by weight of pure ethyl alcohol BG 96 and the whole was heated at 80° C. for further 2 hours.

The solution was then cooled to 40° C. and filtered through a steel filter.

A transparent polyurethane solution containing a di-C$_{12-13}$ alkyl tartrate in isododecane was thus obtained. Such a polyurethane had a molecular weight of 31,500 daltons, a viscosity of 800 mPa*s (at 25° C.) and a concentration of 45.00% by weight.

Example 4

Preparation of a Brilliant Liquid Lipstick

| Components | % by weight |
| --- | --- |
| Phase A | |
| solution of Example 3 | 45.86 |
| trimethylsiloxy phenyl dimethicone | 5.16 |
| trihydroxystearin | 1.96 |
| isohexadecane | 3.53 |
| Phase B | |
| lake RED 7 | 9.18 |
| isododecane | 34.31 |

The fluid lipstick having the aforesaid composition was prepared by dissolving the components of Phase A at 60° C. under stirring for about 15 minutes. Phase B was laminated at room temperature for about 15 minutes and then added to Phase A under stirring until complete dispersion for further 15 minutes.

Example 5

Preparation of a Bright Lip Pencil

| Components | % by weight |
| --- | --- |
| Phase A | |
| polyethylene | 8.41 |
| diisostearyl malate | 51.17 |
| antioxidant | 0.07 |
| Phase B | |
| solution of Example 3 | 32.90 |
| synthetic wax | 2.56 |
| Phase C | |
| disteardimonium hectorite | 0.55 |
| propylene carbonate | 0.11 |
| caprylic/capric triglyceride | 1.53 |
| lake RED 7 CA | 0.86 |
| dicalcium phosphate | 1.84 |

The bright lip pencil having the aforesaid composition was prepared by dissolving the components of Phase A at 120° C. under stirring for about 15 minutes. Phase B was prepared by dissolving the ingredients at 60° C. for about 15 minutes. The ingredients of Phase C were laminated, then Phase A previously added to Phase B was added. An Ultra-Turrax treatment was carried out for further 15 minutes until complete dispersion and homogenization.

Example 6

Preparation of a Brilliant Liquid Eye Shadow

| Components | % by weight |
| --- | --- |
| Phase A | |
| solution of Example 2 | 44.37 |
| trimethylsiloxy phenyl dimethicone | 4.96 |

-continued

| Components | % by weight |
| --- | --- |
| trihydroxystearin | 0.70 |
| isohexadecane | 31.69 |
| Phase B | |
| brown iron oxides | 8.84 |
| isohexadecane | 9.44 |

The brilliant liquid eye shadow having the aforesaid composition was prepared by dissolving the components of Phase A at 60° C. under stirring for about 15 minutes. Phase B was laminated at room temperature for about 15 minutes, then added to Phase A under stirring until complete dispersion and homogenization, for further 15 minutes.

Example 7

Preparation of a Brilliant, Liquid Eye Liner

| Components | % by weight |
| --- | --- |
| Phase A | |
| isododecane | 9.69 |
| dimethicone | 4.15 |
| hydrogenated palm kernel glycerides and hydrogenated palm glycerides | 0.77 |
| sorbitan tristearate | 1.15 |
| phytosteryl isostearate | 0.39 |
| antioxidant | 0.02 |
| preservatives | 0.08 |
| Phase B | |
| trimethylsiloxy silicate | 15.39 |
| Phase C | |
| dimethicone | 6.15 |
| Phase D | |
| disteardimonium hectorite | 2.41 |
| propylene carbonate | 0.80 |
| isododecane | 20.30 |
| ultramarine pigments | 7.10 |
| mica and carmine | 0.79 |
| Phase E | |
| pearls (mica and iron oxides) | 1.58 |
| pearls (mica and titania) | 2.76 |
| mica | 2.96 |
| preservatives | 0.23 |
| Phase F | |
| solution of Example 3 | 23.08 |

The brilliant, liquid eye liner having the aforesaid composition was prepared by heating Phase A, under stirring at 80° C., until completely transparent. Phase B first and then Phase C were added to Phase A at the same temperature. The whole was stirred for about 15 minutes. Phase D was laminated and the laminate was added to the above obtained mixture. The whole was dispersed in tubes, by means of Ultra-Turrax, for about 15 minutes, then Phase E was added and the preparation thus obtained was cooled to about 40° C. under stirring. Phase F was added under stirring and the whole was homogenized and cooled to room temperature.

Example 8

Preparation of Waterproof Eye Mascara

| Components | % by weight |
| --- | --- |
| Phase A | |
| solution of Example 3 | 43.01 |
| trimethylsiloxy phenyl dimethicone | 4.31 |
| Phase B | |
| isododecane | 17.20 |
| disteardimonium hectorite | 3.50 |
| propylene carbonate | 0.70 |
| caprylic/capric triglyceride | 9.78 |
| cosmetic black C33-5000-coloring agent | 17.20 |
| disteardimonium hectorite | 4.30 |

The waterproof eye mascara having the aforesaid composition was prepared by dissolving the components of Phase A at room temperature under stirring for about 5 minutes. Phase B was laminated at room temperature for about 15 minutes, then the laminate was added to Phase A and shaken for about 5 minutes by means of Ultra-Turrax, and stirred until complete dispersion and homogenization.

Example 9

Preparation of a Pigment Coating

| Components | % by weight |
| --- | --- |
| Phase A | |
| pigments (talc-mica-iron oxide) | 85.35 |
| Phase B | |
| solution of Example 1 | 6.10 |
| isododecane | 8.55 |

The coating having the aforesaid composition was prepared by spraying Phase B on Phase A under strong turbulence, drying and retrieving the solvent by oven-drying at 80° C. for 12-24 hours.

Example 10

Preparation of a Foundation

| Components | % by weight |
| --- | --- |
| Phase A | |
| treated talc of Example 9 | 73.6 |
| maize starch | 8.0 |
| zinc stearate | 2.0 |
| pearls (mica and titania) | 3.0 |

-continued

| Components | % by weight |
|---|---|
| preservatives | 0.8 |
| pigments | 5.0 |
| Phase B | |
| pentaerythrityl tetraisostearate | 3.00 |
| octyldodecyl stearoyl stearate | 1.6 |
| dimethicone and dimethiconol | 3.0 |

The foundation having the aforesaid composition was prepared by grinding Phase A in an appropriate grinder for 10 minutes. Phase B was atomized and ground with Phase A for further 5 minutes. Phase C was atomized and ground with the product obtained by grinding Phase A with Phase B. The obtained compound was sieved and compacted.

Example 11

Preparation of a Face Powder

| Components | % by weight |
|---|---|
| Phase A | |
| treated talc of Example 9 | 56.6 |
| maize starch | 8.0 |
| zinc stearate | 2.0 |
| pearls (mica and titania) | 7.5 |
| preservatives | 0.8 |
| pigments | 17.5 |
| Phase B | |
| pentaerythrityl tetraisostearate | 3.00 |
| octyldodecyl stearoyl stearate | 1.6 |
| dimethicone and dimethiconol | 3.0 |

The face powder having the aforesaid composition was prepared by grinding Phase A in an appropriate grinder for 10 minutes. Phase B was atomized and ground with Phase A for further 5 minutes. Phase C was atomized and ground with the product obtained by grinding Phase A with Phase B. The obtained compound was sieved and compacted.

The invention claimed is:

1. A cosmetic composition comprising:
a film-forming agent, wherein the film-forming agent comprises an aliphatic polyurethane in a mixture of organic solvents and cosmetically acceptable ingredients,
wherein said aliphatic polyurethane is obtained by reacting a dialkyl tartrate diol with an aliphatic diisocyanate in an organic solvent,
wherein the dialkyl tartrate diol comprises a dialkyl group,
wherein the dialkyl group comprises at least one selected from the group consisting of a linear alkyl group having from 10 to 20 carbon atoms, a branched alkyl group having from 10 to 20 carbon atoms, and combinations thereof,
wherein the aliphatic diisocyanate is selected from the group consisting of isophorone diisocyanate, 1,6-hexamethylene diisocyanate, and 4,4'-dicyclohexylemethane diisocyanate.

2. The cosmetic composition according to claim 1, wherein said aliphatic polyurethane obtained by reacting said dialkyl tartrate diol, and a natural polyol, with said aliphatic diisocyanate in an organic solvent.

3. The cosmetic composition according to claim 1, wherein the aliphatic polyurethane is obtained by reacting the dialkyl tartrate diol with the aliphatic diisocyanate, at an equivalents ratio from diol and diisocyanate ranging from 1.5 to 0.5.

4. The cosmetic composition according to claim 3, wherein the equivalents ratio from diol and diisocyanate ranges from 1.2 and 0.8.

5. The cosmetic composition according to claim 1, wherein said mixture of organic solvents is selected from the group consisting of a first binary mixture of isododecane and ethanol, a second binary mixture of paraffin and ethanol, and a third binary mixture of isoparaffin and ethanol, and combinations thereof.

6. The cosmetic composition according to claim 5, wherein said mixture of organic solvents comprises the first binary mixture of isododecane and ethanol.

7. The cosmetic composition according to claim 6, wherein said ethanol in said binary mixture is present in an amount from 1% to 15% by weight.

8. The cosmetic composition according to claim 7, wherein said ethanol in said binary mixture is present in an amount of 10% by weight.

9. The cosmetic composition according to claim 1, wherein said dialkyl group of said dialkyl tartrate diol comprises at least one selected from the group consisting of a linear alkyl group having from 11 to 15 carbon atoms, a branched alkyl group having from 11 to 15 carbon atoms, and combinations thereof.

10. The cosmetic composition according to claim 9, wherein said dialkyl group of said dialkyl tartrate diol comprises alkyl groups,
wherein the alkyl groups are different from each other,
wherein the alkyl groups are linear, and
wherein the alkyl groups have from 12 to 13 carbon atoms.

11. The cosmetic composition according to claim 1, wherein said diisocyanate is isophorone diisocyanate.

12. The cosmetic composition according to claim 2, wherein said natural polyol is selected from the group consisting of hydrogenated dilinoleyl alcohol, partially dehydrated and hydrogenated at hydroxylic functionality of 2 castor oil, dimer diol derived from C36 acids and dimerates.

13. The cosmetic composition according to claim 12, wherein said natural polyol is hydrogenated dilinoleyl alcohol.

14. The cosmetic composition according to claim 12, wherein said natural polyol is hydrogenated at hydroxylic functionality of 2 castor oil.

15. The cosmetic composition according to claim 1, wherein said aliphatic polyurethane based on dialkyl tartrate diol is present in an amount of from 25% to 55% by weight.

16. The cosmetic composition according to claim 15, wherein said aliphatic polyurethane based on dialkyl tartrate diol is present in an amount of from 35% to 45% by weight.

17. The cosmetic composition according to claim 1, wherein said organic solvent is isododecane.

18. A method of using the cosmetic composition according to claim 1, comprising incorporating the composition into a cosmetic product for face skin, eyes or lips.

19. The method according to claim 18, wherein said cosmetic product is selected from the group consisting of eye shadow, mascara for eyes, foundation and pigment powders for face and lipsticks.

* * * * *